United States Patent [19]

DeCoster

[11] Patent Number: Plant 6,336

[45] Date of Patent: Oct. 11, 1988

[54] PHILODENDRON PLANT NAMED RED WINE

[76] Inventor: Paul DeCoster, Brusselsesteenweg 94, 9230 Melle, Belgium

[21] Appl. No.: 927,519

[22] Filed: Nov. 6, 1986

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Schwartz, Jeffery, Schwaab, Mack, Blumenthal & Evans

[57] ABSTRACT

A philodendron plant named Red Wine particularly characterized by its very large and round leaves which are grey brown when immature and a very dark green when mature; compact growth habit and form; close and symmetrical internodes on mature plants, rigid stalks and erect leaves on immature plants, and by its efficient propagation by tissue culture.

2 Drawing Sheets

The present invention comprises a new and distinct cultivar of philodendron plant maned Red Wine.

The new cultivar was discovered growing among several hundred random seedlings obtained in approximately September of 1977 from Bamboo Nursery, Opapka, Fla. The plants were approximately 3–4" long with roots, but not rooted in soil, and were indistinguishable one from the other at the time of purchase. The parentage of the new cultivar was not known at the time of acquisition, nor is it now known.

When the seedlings were grown to mature plants by applicant in Melle, Belgium, in the greenhouses of applicant, the novel characteristics of the new cultivar were readily evident. Asexual reproduction by me of the new cultivar by tissue culture beginning in approximately 1982 in Melle, Belgium, and repeated asexual reproduction thereafter, has demonstrated that Red Wine retains its distinctive characteristics through successive propagation.

The following characteristics in combination distinguish Red Wine from other philodendron cultivars of this general type.

1. The leaves are very large and round, having generally the shape of the philodendron cultivar named Pilatonense, illustrated on page 220 of Exotica 3, 1970 Edition, Roehrs Company, East Rutherford, N.J. The leaf shape is very different than the more typical elliptical leaf shape prevalent in many philodendrons.

2. Dark green foliage.

3. Propagates very efficiently by tissue culture, a very important characteristic for commercial philodendrons.

4. Compact growth habit and form, from beginning to maturity, thereby allowing the plant to be sold in 4" and larger pots with the same degree of compactness. It is therefore excellent both for indoor decorating and outdoor planting.

5. Close and symmetrical internodes on mature plants, approximately 4–5 cm apart, thereby providing the compact form indicated. The internode spacing is similar to the well-known cultivar Emerald Duke.

6. Relatively slow grower, reaching approximately 36 inches in diameter and three (3) feet above edge of 25 cm pot in approximately twelve (12) months, starting from a three (3) month old 10 cm plantlet obtained from tissue culture.

7. In immature plants, leaves are relatively erect and carried on rigid stalks thereby making the plant convenient to wrap and ship.

8. The sheathing around the petioles is an attractive, generally deep rose on the exterior to a light rose pink.

9. No flowers to date have been noted.

10. The edges of the leaves have a clearly visible but very narrow band, less than 1 mm, around the entire edge, with the band appearing to be translucent infused with a brown-rose color.

In the accompanying color photographic drawings, sheet 1 is a top perspective view of a plant of Red Wine, approximately ten (10) months old. Sheet 2 is a close up perspective view of Red Wine, showing more clearly its compact form and foliage colors.

The following observations and measurements are based on plants of Red Wine twelve (12) months in age grown in Melle, Belgium in greenhouses in accordance with standard commercial practices. Color values are based on The Royal Horticultural Society Colour Chart (R.H.S.), with the color values being taken in mid-September at approximately 10:00 a.m. under natural light conditions.

FORM CHARACTERISTICS

Leaf shape:

*Mature.*—Generally round, with bottom of leaf being concavely shaped at petiole connecter; undulating or wavy in direction of length, particularly at edge.

*Immature.*—Generally ovate, with bottom of leaf at petiole connector being essentially a continuous edge or slightly concave.

*Tip.*—Cuspidate.

*Base.*—Concavely shaped relative to rib; auriculate.

*Margin.*—Smooth, with the edges of the leaves having a very narrow but visible band (less than 1 mm) around the entire edge.

*Venation.*—Present.

Leaf attachment: Stalked.

Leaf arrangement: Alternate.

Petiole: Rigid, extending generally more vertical than horizontal in center of plant; normally grooved except occasionally flat on inner surface.

Internode spacing: About 5–6 cm on mature plant at top.

Overall appearance: Generally vertical, normally several plants per pot, supported by a moss stick.

SIZE CHARACTERISTICS OF TYPICAL COMMERCIAL PLANT

Leaf:

*Width at widest point:* 27–28 cm.

*Width 1" from top:* 10–11 cm.

*Length:* 34–36 cm from tip to tip concave base.

Petiole:

*Length.*—30–33 cm for mature leaves.

*Diameter (center).*—Approximately 1.5 cm.

*Internode spacing.*—1 cm.

Stem diameter.—Approximately 3–4 cm.

COLOR CHARACTERISTICS

Leaf:

*Mature.*—Top, very dark green, darker than 147A. Under surface 148A infused around edges and center vein with approximately 183B; midvein infusion more green than 183B.

*Immature.*—Top, no precise color when first unfolding, but 199A is closest, gradually darkening to mature colors indicated; under surface 177C-D.

*Intermediate (between mature and immature).*—In transition from immature to mature, leaf color becomes very dark green infused with slight brown so as to give a deep green, much darker than 147A; underside closest to 199B-C, with red-purple veins.

*Venation.*—Midrib, 147B; veins, 147B.

Petiole: 176A where petiole is flat on one side; where petiole is grooved, outside groove color is darker than 199A; inside of groove, close to 199B; immature petiole color 183B.

I claim:

1. A new and distinct philodendron plant named Red Wine, as described and illustrated, and particularly characterized by its very large and round leaves which are grey brown when immature and a very dark green when mature; compact growth habit and form; close and symmetrical internodes on mature plants, rigid stalks and erect leaves on immature plants, and by its efficient propagation by tissue culture.

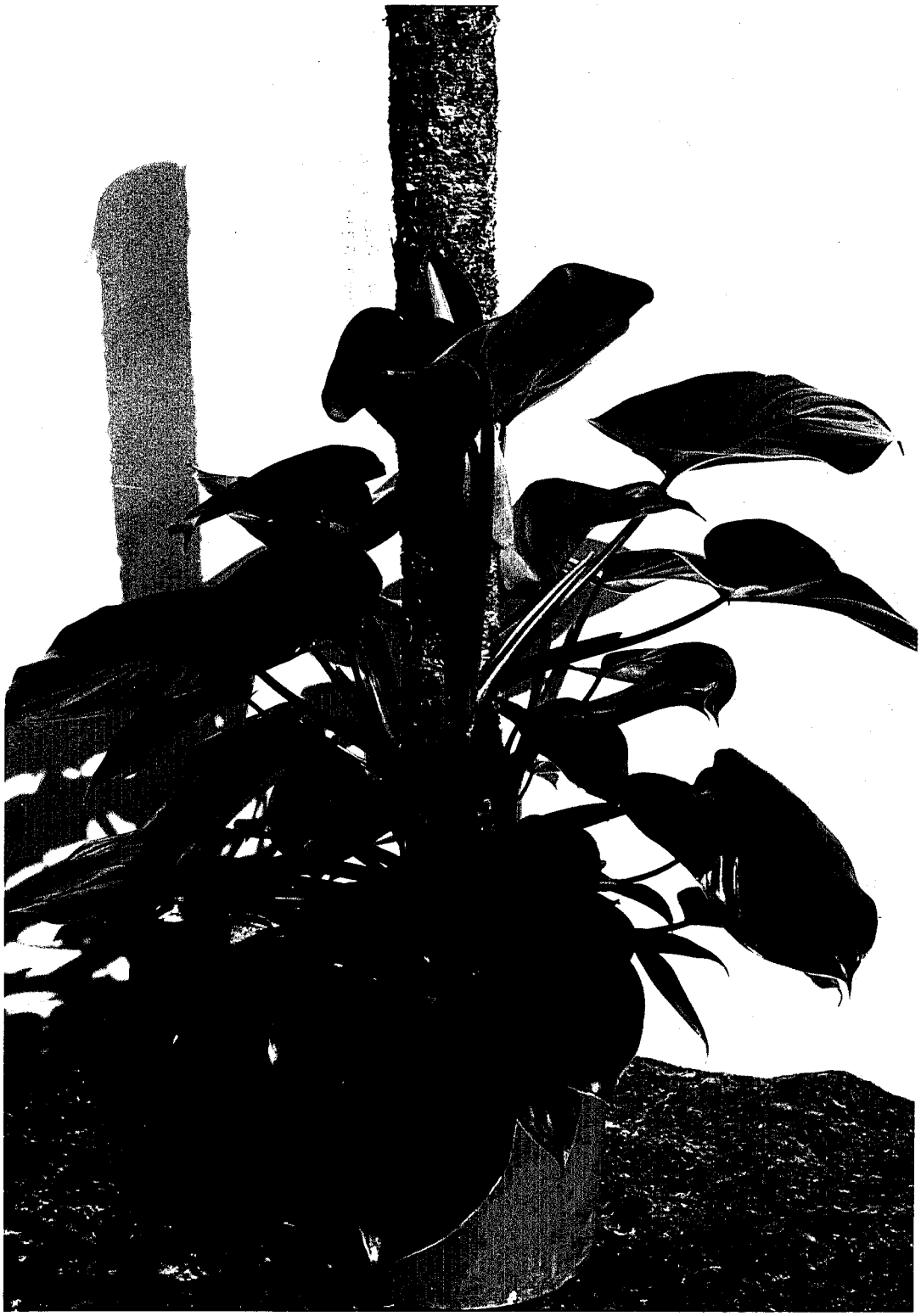

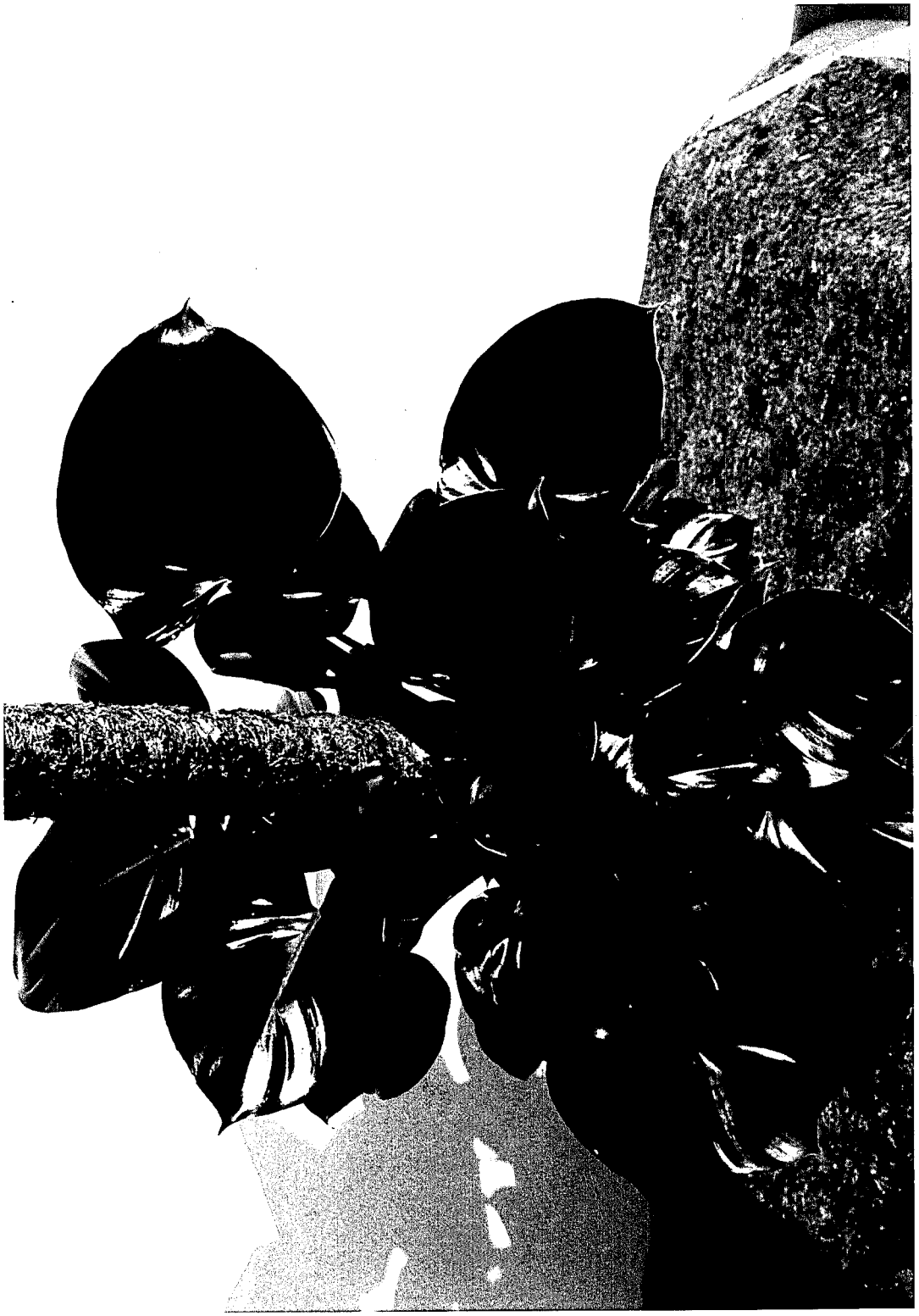

* * * * *